United States Patent [19]

Annand

[11] Patent Number: 4,815,468
[45] Date of Patent: Mar. 28, 1989

[54] SUTURELESS CLOSURE

[76] Inventor: David S. Annand, Box 31, R.D. #1, Landenberg, Pa. 19350

[21] Appl. No.: 1,908

[22] Filed: Jan. 9, 1987

[51] Int. Cl.[4] .............................................. A61B 17/04
[52] U.S. Cl. .................................................. 128/335
[58] Field of Search ................................ 128/335, 337

[56] References Cited

U.S. PATENT DOCUMENTS

| | | | |
|---|---|---|---|
| 363,538 | 5/1887 | Penny | 128/335 |
| 1,074,413 | 9/1913 | DeBaun et al. | 128/335 |
| 1,428,495 | 9/1922 | Radcliffe | 128/335 |
| 1,774,489 | 8/1930 | Sarason | 128/335 |
| 1,969,188 | 8/1934 | Spicer | 128/335 |
| 2,196,296 | 4/1940 | Flynn . | |
| 2,303,131 | 11/1942 | Morgan | 128/335 |
| 2,371,978 | 3/1945 | Perham | 128/335 |
| 2,387,131 | 10/1945 | Fernandez | 128/335 |
| 2,409,261 | 10/1946 | Dow . | |
| 3,068,870 | 12/1962 | Levin | 128/337 |
| 3,103,218 | 9/1963 | Ajemian | 128/335 |
| 3,487,836 | 1/1970 | Niebel et al. | 128/335 |
| 3,698,395 | 10/1972 | Hasson | 128/335 |
| 3,789,851 | 2/1974 | LeVeen | 128/335 |
| 3,863,640 | 2/1975 | Haverstock | 128/335 |
| 3,926,193 | 12/1975 | Hasson . | |
| 3,971,384 | 7/1976 | Hasson . | |
| 3,983,878 | 10/1976 | Kawchitch | 128/335 |
| 4,423,731 | 1/1984 | Roomi | 128/335 |
| 4,526,173 | 7/1985 | Sheehan | 128/335 |
| 4,535,772 | 8/1985 | Sheehan | 128/337 |
| 4,539,990 | 9/1985 | Stivala | 128/335 |
| 4,605,005 | 8/1986 | Sheehan | 128/335 |

FOREIGN PATENT DOCUMENTS 692496  7/1965  Italy .................................. 128/335

Primary Examiner—Richard C. Pinkham
Assistant Examiner—Gary Jackson
Attorney, Agent, or Firm—Connolly and Hutz

[57] ABSTRACT

A non-invasive closure functions to draw together and close the open edges of a wound while retaining such edges in an approximated and everted condition during the healing process. The closure comprises a pair of base plates having inner and outer edges as well as structure for securing these plates along opposite sides of a wound with the inner edges thereof parallel to one another and in close proximity to the wound. One of a pair of operator elements is connected at its inner end to one of the base plates at the inner edge thereof and the other element is similarly connected to the other base plate. Each operator element extends upwardly and outwardly away from its respective base plate at an angle greater than 90° so that the operator elements are angled toward one another before the wound is closed. Cooperative fastening structure on the operator elements functions to hold them in generally parallel mutually engaging relationship when the elements are urged together to close the wound. Such urging causes the inner edges of the base plate to shift toward one another to thereby close the wound and also to move in an outward direction to thereby evert the edges of the wound.

14 Claims, 2 Drawing Sheets

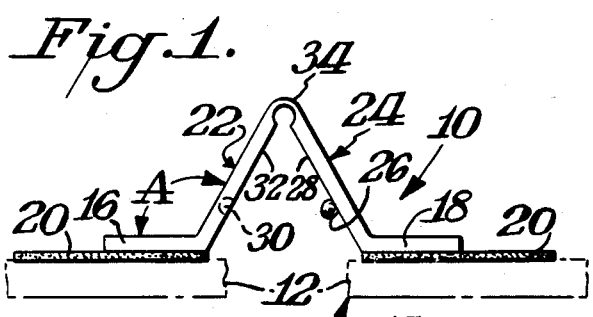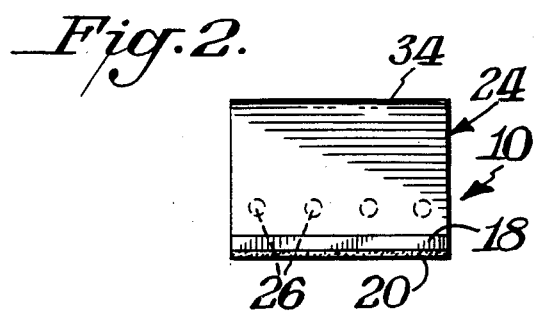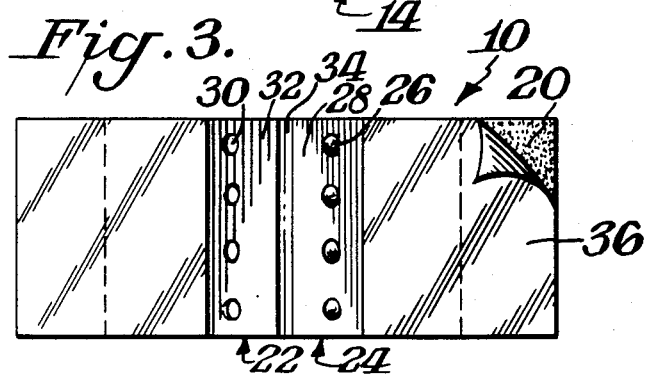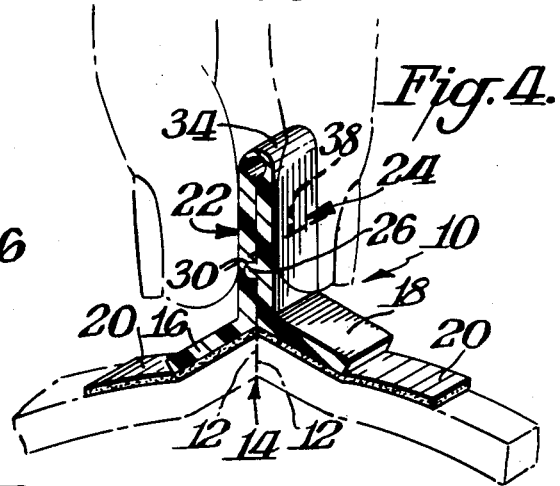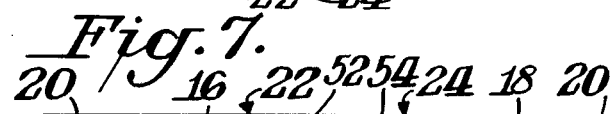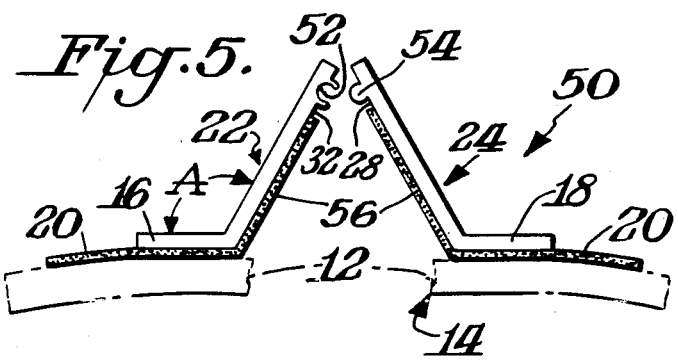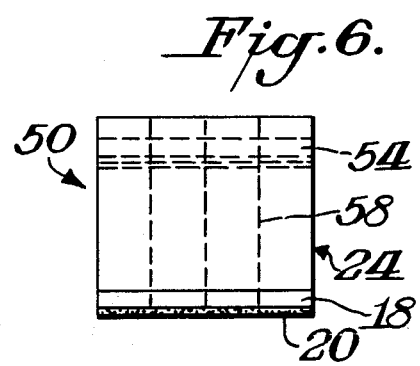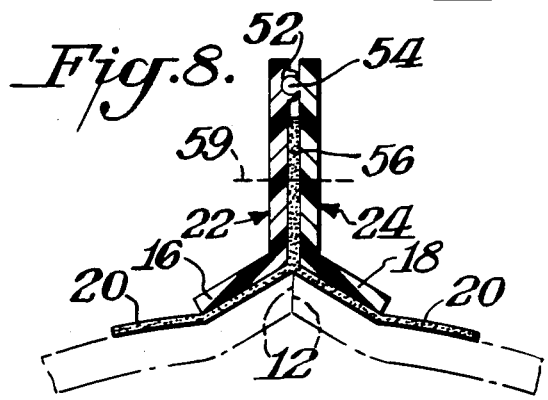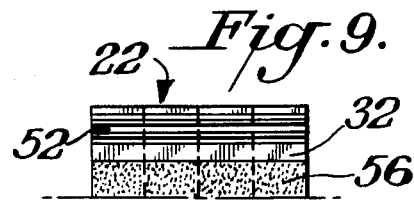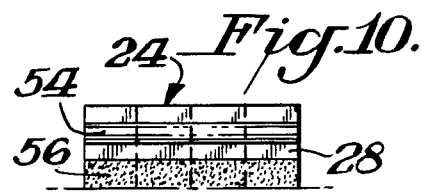

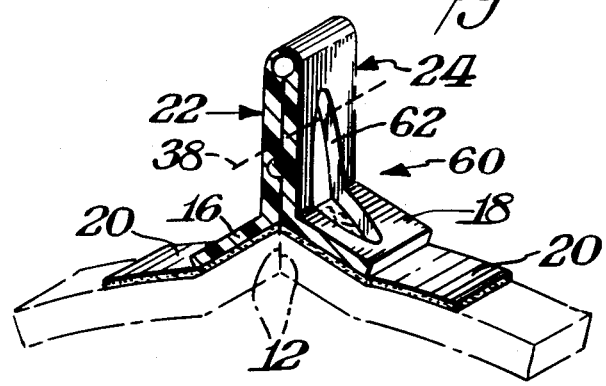

SUTURELESS CLOSURE

BACKGROUND OF THE INVENTION

The present invention relates to a wound closure, and more particularly to a sutureless closure that functions to draw together and close the open edges of a wound while retaining such edges in an approximated and everted condition during the healing process.

Prior to the present invention, numerous closure devices have been proposed for closing wounds and the like. Such devices range from simple adhesive backed material to somewhat more complicated arrangements such as those described in U.S. Pat. Nos. 3,863,640, 4,526,173 and 4,535,772.

Lacings and/or ties of a variety of shapes and sizes have long been utilized to draw together and retain the edges of a wound and thereby eliminate the need for sutures. Lacings in the wound area often cause infection and scarring, and they do not function to evert the edges of the wound. Arrangements that include such lacings and/or ties are described in U.S. Pat. Nos. 345,541, 363,538, 1,074,413, 1,428,495, 1,774,489, 1,969,188, 2,196,296, 2,303,131, 2,387,131, 2,409,261, 3,103,218, 3,698,395, 3,926,193, 3,971,384, 3,983,878 and 4,423,731, for example. Also, Italian Patent 692,466 granted July 27, 1965 relates to this general type of closure.

For the most part, the heretofore proposed sutureless closures do not evert the edges of the wound when such edges are drawn together for closing. Non-eversion of the edges is a disadvantage since good approximation of the skin layer alignment is not achieved and infection and scarring often results. While U.S. Pat. No. 4,539,990 does explain a sutureless closure that everts the edges of a wound upon closure, the adjustable clips unduly complicate the construction.

SUMMARY OF THE INVENTION

Accordingly, an object of the present invention is to avoid the disadvantages of the prior art by providing a sutureless closure comprising relatively few component parts all of which function in an easy and effective manner to draw together and close the open edges of a wound while retaining such edges in an everted position during the healing process.

In accordance with the present invention, a sutureless closure is provided for drawing together and closing the open edges of a wound while retaining such edges in an approximated and everted condition during the healing process. In its simplest form, the closure herein comprises a pair of base plates, each having inner and outer edge portions as well as structure for securing the plates along opposite sides of the wound so that the inner edge portions thereof are generally parallel to one another and in close proximity to the wound. One of a pair of operator elements is connected at its inner end to one of the base plates at the inner edge portion thereof while the other element is similarly connected to the other base plate. Each operator element extends upwardly and outwardly away from its respective base plate at an angle greater than 90° so that the operator elements are angled toward one another prior to closing the wound. Cooperative fastening structure on the operator elements is constructed and arranged to hold them in generally parallel mutually engaging relationship when the elements are urged together to close the wound. This particular movement of the operator elements causes the inner edge portions of the base plate to shift toward one another to thereby close the wound and also to move in an outward direction to thereby evert the edges of the wound.

Preferably, each operator element is integrally connected to its respective base plate. Also, in one embodiment of the present invention, the operator elements are integrally connected together along a live hinge line at the outer ends thereof to thereby insure excellent approximation of the edges of the wound. In another embodiment, each operator element and its respective base plate are separate from the other operator element and base plate. In the latter embodiment a continuous channel may be provided on one element with a complimentary elongated bead on the other element in alignment with the channel and constructed for locking engagement therewith. This feature also insures excellent approximation of the wound edges.

In the preferred embodiments of the present invention, the base plates and operator elements are generally planar in configuration, and the means securing the base plate on opposite sides of a wound comprises adhesive material. The base plates and operator elements are preferably fabricated of thermoplastic material, although other materials are equally suitable.

The angle between each base plate and its respective upwardly and outwardly extending operator element is in the range of about 110°–130°, and preferably about 120°.

The cooperative fastening structure on the operator elements may include adhesive material on the inside surfaces of the elements. Other fastening structure may be used such as protuberances on one of the operator elements with complimentary sockets on the other element constructed and arranged to receive the protuberances in locking engagement.

In one embodiment of the present invention, the base plates and operator elements include open interior portions arranged to provide a window for viewing of a wound when the closure is in place. Such open portions also allow air to circulate and assist in the healing process.

BRIEF DESCRIPTION OF THE DRAWING

Novel features and advantages of the present invention in addition to those mentioned above will become apparent to persons of ordinary skill in the art from a reading of the following detailed description in conjunction with the accompanying drawing wherein similar reference characters refer to similar parts and in which:

FIG. 1 is a side elevational view of a sutureless closure according to the present invention;

FIG. 2 is a right side elevational view of the sutureless closure shown in FIG. 1;

FIG. 3 is a bottom plan view of the sutureless closure shown in FIG. 1;

FIG. 4 is a sectional perspective view illustrating the sutureless closure of FIGS. 1-3 in an operative position with the open edges of a wound approximated, drawn together, everted and retained closed;

FIG. 5 is a side elevational view of another sutureless closure according to the present invention;

FIG. 6 is a right side elevational view of the sutureless closure in FIG. 5;

FIG. 7 is a top plan view of the sutureless closure shown in FIG. 5;

FIG. 8 is a sectional view of the sutureless closure shown in FIGS. 5–7 in an operative position with the open edges of a wound drawn together, everted and retained closed;

FIG. 9 is a fragmental side elevational view of the inside surface of the left hand operator element shown in FIG. 5;

FIG. 10 is a fragmental side elevational view of the inside surface of the right hand operator element shown in FIG. 5; and FIG. 11 is a view similar to FIG. 4 but illustrating a sutureless closure having a window therein for viewing the wound during closure thereof and during the healing process.

DETAILED DESCRIPTION

Referring in more particularity to the drawings, FIGS. 1–4 illustrate a non-invasive sutureless closure 10 for drawing together and closing the open edges 12 of a wound 14 while retaining such edges in an approximated and everted condition during the healing process. Closure 10 comprises a pair of base plates 16, 18 with adhesive material 20, 20 suitably attached thereto for securing the base plates along opposite sides of wound 14 so that the inner edge portions of the plates are generally parallel to one another and in close proximity to the wound. This particular relationship is shown best in FIG. 1. Closure 10 also includes a pair of operator elements 22, 24 with element 22 connected at its inner end to base plate 16 at the inner edge portion thereof and element 24 similarly connected to base plate 18.

The angular relationship between each base plate and its respective operator element is an important feature of the present invention in that it contributes to eversion of the wound edges 12 when closure 10 is manipulated to its operative position, such as shown in FIG. 4. Specifically, each operator element 22, 24 extends upwardly and outwardly away from its respective base plate at an angle A greater than 90°. With this relationship, operator elements 22, 24 are angled toward one another before the wound is closed, as best shown in FIG. 1. The angle between each base plate and its respective upwardly and outwardly extending operator element is in the range of about 110°–130°, and preferably about 120°.

Cooperative fastening structure is positioned on operator elements 22, 24 for holding them in generally parallel mutually engaging relationship when these elements are urged together to close the wound. In the embodiment of the invention illustrated in FIGS. 1–4, the cooperative fastening structure comprises a series of protuberances 26 on inside surface 28 of element 24. Complimentary sockets 30 are located on inside surface 32 of element 22. These sockets are constructed and arranged to receive protuberances 26 in locking engagement to thereby hold operator elements 22, 24 in generally parallel engaging relationship when the elements are urged together to close the wound, as shown best in FIG. 4. In sutureless closure 10, the operator elements are integrally connected together along a live hinge line 34 at the outer ends of the elements. The hinge line assists in alignment of protuberances 26 and sockets 30 and also provides a one-piece construction for ease of use of closure 10. More importantly, hinge line 34 aligns the base plates and wound edges which results in excellent approximation of the wound edges.

Preferably, sutureless closure 10 is fabricated from thermoplastic material such as polyethylene or polypropylene, for example. Absolute rigidity is not a requirement, and preferably the overall closure construction is somewhat flexible but capable of maintaining the angular relationship between base plates 16, 18 and operator elements 22, 24. Also, adhesive material 20, 22 may be covered with appropriate strippable backing 36 on the exposed surfaces thereof.

Sutureless closure 10 is used in the following manner. First, the length of wound 14 is determined and a closure having a similar length is selected. In the embodiment of FIGS. 1–4, the closure includes four protuberances 26 on operator element 24, but other lengths are also within the scope of the present invention. For example, if the wound is half the size of wound 14, closure 10 can simply be cut in half with a pair of scissors or knife. Following selection of a proper length closure, strippable backing 36 is removed from one of the base plates 16 or 18, and that plate is anchored in place in close proximity to the wound. Next, the remaining base plate is anchored in place in similar fashion. Operator elements 22, 24 are then grasped between the fingers and urged together along hinge line 34 thereby insuring excellent approximation while drawing together and closing open edges 12 of wound 14. Protuberances 26 enter sockets 30 to fasten the operator elements together in generally parallel mutually engaging relationship, as shown in FIG. 4.

Such urging of the operator elements causes the inner edge portions of the aligned base plates to shift foward one another and thereby close the wound since these plates are annexed on opposite sides of the wound. Additionally, due to the angular relationship between each base plate and its respective operator element, the inner edge portions of the plates also shift in an outward direction to thereby evert side edges 12 of wound 14, as best shown in FIG. 4. This maneuver produces good approximation of skin layer alignment which results in excellent healing without significant risk of infection or scarring.

Another feature of closure 10 is that the operator elements may be slightly spread apart after the closure is in place by simply urging the protuberances out of their respective sockets. This allows inspection of the wound site when desired. Upon completion of such inspection, the operator elements are returned to their parallel positions. Moreover, the outer portions of the operator elements may be trimmed away along cut line 38.

FIGS. 5–10 illustrate another embodiment of the present invention, and similar parts have been identified with similar reference characters. Non-invasive sutureless closure 50 is different from closure 10 in that each operator element and its respective base plate are separate from the other operator element and base plate. In essence, there is no integral hinge line of the type 34 of closure 10.

Closure 50 includes a continuous channel 52 on operator element 22 and an elongated complimentary bead 54 on element 24 in alignment with the channel. Bead 54 is constructed and arranged for locking engagement within the channel to insure alignment of the base plates and excellent approximation of the wound edges. This arrangment also functions to hold the operator elements in generally parallel mutually engaging relationship when the elements are urged together to close the wound. The cooperative fastening structure on the operator elements may include on inside surfaces 28, 32 adhesive material 56 to hold the elements together when the wound in closed.

Closure 50 includes spaced apart score lines 58 along the length thereof for selecting a proper length necessary for a particular wound. While these score lines assist in dividing the closure, the overall integrity and strength of the closure is not adversely affected by these lines.

Use of closure 50 is similar to that of closure 10. One of the base plates is initially anchored in place in close proximity to the wound, and the other plate is anchored on the opposite side of the wound. Bead 54 is snapped into channel 52 to insure excellent approximation of the wound edges, and the operator elements 22, 24 are then urged together until they are in parallel mutually engaging relationship. Adhesive 56 together with the locking action of channel 52 and bead 54 hold the operator elements together. Side edges 12 of wound 14 are closed and everted, as best shown in FIG. 8. A portion of the operator elements may then be cut away such as along line 59.

FIG. 11 illustrates an alternate embodiment of the invention similar in many respects to closure 10 of FIGS. 1-4. In essence, FIG. 11 shows a non-invasive sutureless closure 60 having open interior portions 62 in base plates 16, 18 and operator elements 22, 24. These open interior portions provide a window for viewing of wound 14 after closure 60 is in place. Additionally, openings 62 enable the circulation of air to assist the healing process.

What is claimed is:

1. A sutureless closure for drawing together and closing the open edges of a wound while retaining such edges in an approximated and everted condition during the healing process, the closure comprising a pair of base plates each having inner and outer edge portions, means for securing the base plates along opposite side of a wound with the inner edge portions thereof generally parallel to one another and in close proximity to the wound, a pair of operator elements each having inner and outer ends, one operator element connected at its inner end to one of the base plates at the inner edge portion thereof and the other element similarly connected to the other base plate, each operator element extending upwardly and outwardly away from its respective base plate at an angle greater than 90° whereby the operator elements are angled toward one another before the wound is closed, and fastening structure for holding the operator elements in generally parallel mutually engaging relationship with one another when the elements are urged together to close the wound, such urging causing the inner edge portions of the base plates to shift toward one another to thereby close the wound and also to move in an outward direction to thereby evert the edges of the wound.

2. A sutureless closure as in claim 1 wherein each operator element is integrally connected to its respective base plate.

3. A sutureless closure as in claim 1 wherein the operator elements are integrally connected together along a live hinge line at the outer ends thereof.

4. A sutureless closure as in claim 1 wherein each operator element and its respective base plate are separate from the other operator element and base plate.

5. A sutureless closure as in claim 1 wherein the base plates and operator elements are generally planar.

6. A sutureless closure as in claim 1 wherein the means securing the base plates on opposite sides of a wound comprises adhesive material.

7. A sutureless closure as in claim 1 wherein the base plates and operator elements are fabricated of thermoplastic material.

8. A sutureless closure as in claim 1 wherein the angle between each base plate and its respective upwardly and outwardly extending operator element is in the range of about 110°-130°.

9. A sutureless closure as in claim 8 wherein the angle is about 120°.

10. A sutureless closure as in claim 1 wherein the operator elements include inside surfaces that face one another, and the fastening structure for holding the operator elements together includes adhesive material on the inside surfaces thereof.

11. A sutureless closure as in claim 1 wherein the fastening structure for holding the operator elements together includes at least one protuberance on one operator element and at least one complimentary socket on the other element constructed and arranged to receive the protuberance in locking engagement therewith to thereby hold the operator elements in generally parallel mutually engaging relationship when they are urged together to close the wound.

12. A sutureless closure as in claim 11 including a series of spaced apart protuberances on one operator element and an equal number of sockets on the other element in alignment with the protuberances.

13. A sutureless closure as in claim 4 including a continuous channel on one operator element and an elongated complimentary bead on the other operator element in alignment with the continuous channel constructed and arranged for locking engagement within the channel.

14. A sutureless closure as in claim 1 wherein the base plates and the operator elements include open interior portions constructed and arranged to provide a window for viewing of a wound when the closure is in place.

* * * * *